(12) United States Patent
Merrett et al.

(10) Patent No.: US 7,081,091 B2
(45) Date of Patent: Jul. 25, 2006

(54) DATA ANALYSIS SYSTEM

(75) Inventors: Philip Jonathan Merrett, Hampshire (GB); Loua Asad-Hanna Al Shaikh, Surrey (GB)

(73) Assignee: QinetiQ Limited, London (GB)

( * ) Notice: Subject to any disclaimer, the term of this patent is extended or adjusted under 35 U.S.C. 154(b) by 54 days.

(21) Appl. No.: 10/230,395

(22) Filed: Aug. 29, 2002

(65) Prior Publication Data

US 2003/0225315 A1    Dec. 4, 2003

(30) Foreign Application Priority Data

May 31, 2002   (GB)   .................................. 0212700

(51) Int. Cl.
*A61B 5/00*    (2006.01)
(52) U.S. Cl. ..................................... 600/300; 128/920
(58) Field of Classification Search ........ 600/300–301, 600/508–509, 523–525; 128/920–925, 904, 128/903; 340/501, 540, 573.1, 995.15, 539.1; 345/530; 705/2–4; 379/106.1–2; 700/83
See application file for complete search history.

(56) References Cited

U.S. PATENT DOCUMENTS

| | | | |
|---|---|---|---|
| 5,355,889 A |  | 10/1994 | Nevo et al. |
| 5,830,150 A | * | 11/1998 | Palmer et al. ............... 600/523 |
| 5,921,920 A | * | 7/1999 | Marshall et al. ............ 600/300 |
| 6,322,502 B1 | * | 11/2001 | Schoenberg et al. ........ 600/300 |

OTHER PUBLICATIONS

International Search Report dated Oct. 19, 2004.
Evaluation of a PC-Based Program for Rapid Bedside Calculation of Ten Severity Scores in the ICU, A. Nierhaus, et al., Oct. 18, 2000, XP-002298699.
XP-002298700, Network Computer Status-Gantt Load Chart, Mar. 23, 2002.
The SOFA (Sepsis-related Organ Failure Assessment) score to describe organ dysfunction/failure, Intensive Care Medicine, vol. 22, No. 7, Jul. 1996, XP-009037295, Vincent et al.
A Real-Time Status Monitor as a Tool for Operating Rom Management, Feb. 18, 2001, XP-002298701, Eaton et al.

* cited by examiner

*Primary Examiner*—Max F. Hindenburg
*Assistant Examiner*—Michael Astorino
(74) *Attorney, Agent, or Firm*—Nixon & Vanderhye P.C.

(57)    ABSTRACT

A system and method for gathering and displaying information in data intensive environments. It is particularly concerned with data analysis in a critical care environment to provide a graphical display of derived information, comprising a series of bar charts representative of a corresponding series of functions. Each bar chart comprises a linear series of time-divided segments wherein each segment of each bar chart is assigned a colour corresponding to the status of that function. The status of each function is derived by scoring contributory data indicators in accordance with pre-set threshold values, and logically combining to produce a status score for each function. Interventions that affect particular functions may also be recorded and displayed against those functions so that their effect is readily discernible.

22 Claims, 6 Drawing Sheets

DATA ANALYSIS SYSTEM

TECHNICAL FIELD

This invention relates generally to systems and methods for information analysis in data intensive environments and to applications thereof for use as an aid in making decisions. It is particularly concerned with data analysis in a critical care environment.

BACKGROUND

Whilst computerisation has clearly been beneficial to numerous aspects of modern life, its increasing use in data capture has given rise to a new problem. Automated monitors and measuring systems can take readings more frequently than was possible with their manually operated predecessors. Whenever a decision or assessment is to be made based on the readings from these systems, there is accordingly a vast amount of data available. The sheer volume of data alone may obscure judgment but, more often than not, the assessment must also be made rapidly. Such situations will be referred to as data intensive environments.

One example of a data intensive environment is that encountered in a hospital, in particular in intensive care and high dependency units. Current clinical practice requires that a plethora of specific medical data are measured in the critically ill patient. Different data are collected at various intervals and are traditionally entered onto large paper-based observation charts. Psychological studies have shown that the normal human brain can handle some 20 variables at any one time. There is thus always a danger of information overload, even for skilled staff. Each patient's paper chart must be studied carefully in order to detect important changes in his or her condition. Unfortunately, there is often only recognition of an acute system failure once an adverse trend has been established.

There is now the added complication that newer technological advances have allowed closer monitoring of a patient, for example heart rate and blood pressure changes may now be recorded every few seconds; this has also increased the contribution to the data burden. Although theoretically therefore, such close monitoring may allow early detection of adverse trends so that prompt early corrective measures may be instituted, in practice the amount of data often makes its interpretation more difficult.

The clinical environment is rife with distractions which often put staff under extreme pressure; this is particularly exacerbated with the high level of alarms. Moreover, the level of expertise amongst clinicians for signal interpretation can vary considerably, with the lesser skilled staff more likely to make errors in diagnosis and selection of the most appropriate treatment. Particularly where it is necessary for staff to assess medical data by referring to known organ system failure scoring systems, lesser skilled staff are more likely to make an inaccurate assessment of the patient's condition, or to take longer to recognise an adverse trend.

A further problem is that the data available needs to be assessed having regard to recent clinical interventions, which interventions have traditionally only been recorded by nursing staff as hand annotations to paper charts.

U.S. Pat. No. 5,921,920 to Marshall et al. describes a patient monitoring system, which creates graphical displays of pulmonary and other patient functions in order better to present a wealth of information to the clinician. In a preferred display, eight principal variables are displayed radially, with their arrangement and size intended to assist the clinician. This prior art system, although capable of providing a sophisticated modelling capacity, does not display the overall patient status in such a way as to be readily intelligible by lesser skilled staff (or indeed, relatives of patients); nor does it display interventions or facilitate an assessment of their effect on related organ systems.

There is therefore a perceived need to provide a system which assists an assessor in making a judgment based on analysis of large amounts of data, by enabling an increase in the speed with which the judgment is reached and potentially improving the accuracy of the diagnosis. In particular, in the field of critically ill patient care, there is a perceived need for a system with which regularly-collected patient data can be distilled to provide a reduced data set from which an assessment of patient condition can more readily be made.

SUMMARY

The present invention provides a method of analysis of data measured in an environment, the method comprising the steps of:
(a) Gathering data, generated at selected time intervals, from monitoring equipment and/or personnel;
(b) Comparing each data item gathered at Step (a) with preset threshold values;
(c) For each of a selected group of functions, each function having a status which is contributory to an overall status of the environment and the number of functions in the group being less than the number of data items, scoring each function on the basis of the comparisons made at Step (b) for all data items indicative of the status of that function;
(d) Converting scores obtained at Step (c) to one of a number of selected visual representations and assigning those representations to correspondingly scoring functions for a specific time period,
(e) Displaying a series of graphical representations on a display screen, wherein each graphical representation corresponds to one of the group of functions and comprises a series of time-divided segments arranged sequentially, and wherein each segment corresponding to the time period on each graphical representation is visually represented according to the visual representation assigned to the corresponding function at Step (d); and
(f) Repeating steps (a) to (e) for an adjacent time period, whilst preserving the segment's visual representation for at least one previous time period.

Different types of data may be gathered at different intervals depending on their respective availability. The time periods into which the displayed segments are divided are preferably adjustable to allow a user to adjust the display. Hence, the time periods will not usually match the sampling intervals of the data, in which case the last available data will have to be used. Where the display time period is altered by the user, the status of each function for each new segment is recalculated.

The graphical representation may comprise any suitable method of display, providing that it extends along a time line and is formed of time-divided segments arranged adjacent or close to one another in time order. Usually, a bar chart of straight, parallel bars (or thick lines) will be most appropriate, as this has been found to be the most readily intelligible display format. However, other arrangements such as straight or curved lines, usually arranged parallel to one another and representing the various functions may be used as well. Circles divided into respective sectors with a circumference representing the timeline may also be appropriate, for example where only a few functions are being monitored.

The visual representation found to be the most effective is the use of different colours. For example, any functions at a critical level could be represented in red or orange colours, while other colours, possible matching the order of the spectrum, can portray increasingly less critical levels. However, different forms of hatching, different tones (i.e. light to dark variations), or, for example, merely labelling with alphanumeric characters may also be employed. The respective functions may be distinguished from one another by a secondary visual indication. For example, where hatching or tonal differences are employed to denote status, the respective functions can be distinguished from one another by being different colours, and vice versa.

In an important aspect of the present invention, there is recorded in the above method one or more interventions conducted upon, and capable of affecting, the environment, the method further comprising displaying on the display screen the one or more interventions adjacent to one or more of the segments corresponding to the time of the intervention and/or adjacent to a timeline corresponding to the time-divided segments, so as to facilitate a comparison of the effect of the intervention on the environment.

This aspect is of particular value in medical applications, where the data relates to the physical condition of a patient.

The intervention may be displayed against the segments of one or more, and preferably all, of the functions that it is capable of affecting. Importantly, this allows a user at a glance to recognise whether the intervention has had an impact on the related functions. The intervention is usually displayed as selected details and/or as a marker. Where a marker is solely employed, further details of the intervention are preferably accessible for display by the user.

Advantageously, a protocol by which an intervention is conducted is additionally recorded and is displayed or accessible for display by the user. The protocols may be pre-grouped to a particular function, for example an organ system in medical applications, so that the intervention can be displayed against the functions (e.g. organ systems) it affects. Alternatively, the intervention can designate the functions it affects when it is first entered. Either way, it is advantageous to have a default setting whereby the intervention is indicated next to a general timeline or general condition indicator.

As a result of the above, the invention is able to provide a real-time single-screen display that allows direct comparison of the functions of the environment and their correlation with any interventions performed.

The present invention further provides a method of analysis of data measured in a time-varying environment, the method comprising the steps of:
(a) Gathering data, generated during a selected time period, from monitoring equipment and/or personnel;
(b) Comparing each data item gathered at Step (a) with preset threshold values;
(c) For each of a selected group of functions, each function having a status which is contributory to an overall status of the environment and the number of functions in the group being less than the number of data items, scoring each function on the basis of the comparisons made at Step (b) for all data items indicative of the status of that function;
(d) Converting scores obtained at Step (c) to a colour representation and assigning these colours to correspondingly scoring functions at the time period,
(e) Displaying a series of bar charts on a display screen, wherein each bar chart corresponds to one of the group of functions and comprises a linear series of time-divided segments, and wherein each segment corresponding to the time period on each bar chart is coloured with the colour assigned to the corresponding function at Step (d); and
(f) Repeating steps (a) to (e) for an adjacent time period, whilst preserving bar chart segment colouration for at least one previous time period.

In this aspect bar chart segment colouration is preferably preserved for at least eight previous time periods, particularly where those are one hour periods. Typically, it will be useful to preserve such information for the previous 4, 8, 12 or 24 hours.

Although the manner of collection of data is not a part of this invention and may be entirely manually input data, more usually automatically monitoring equipment will supply most or all of the data.

In a second aspect, the present invention provides a computer system configured:
to provide a graphical display of derived information, the display comprising a series of bar charts representative of a corresponding series of functions, each bar chart comprising a linear series of time-divided segments wherein each segment of each bar chart is one of a set of permitted colours,
to assign the colours to the segments in accordance with the status of the corresponding function at the time period represented by that segment
to derive the status of each function from a number of data indicators extracted from a database wherein each data indicator comprises an experimental observation made on a system at a time corresponding to the time period represented in the bar chart by the relevant segment, and the status of each function is derived by scoring contributory data indicators in accordance with preset threshold values to produce a status score for each function.

In an alternative aspect the present invention provides a monitoring system which graphically displays derived information, the system comprising:
monitoring equipment arranged to make periodic observations on a system,
a database arranged to store as data items results of periodic observations made by the monitoring equipment,
a processor arranged to analyse periodically the stored data items to provide an indication as to status of a selected group of functions, the status of each function being deducible as a score from a subset of the data items compared with preset threshold values, and
a display means arranged to display a series of bar charts representative of the group of functions, each bar chart comprising a linear series of time-divided segments wherein each segment of each bar chart is one of a set of permitted colours, the colours being assigned to the segments in accordance with the score obtained for the corresponding function at the time period represented by that segment.

The monitoring system preferably also includes a manual data input arranged to write information to the database in the form of data items, these data items corresponding to results of manual observations made on the system.

In a fourth aspect, the invention provides a computer readable medium embodying instructions for execution by a processor, the computer readable medium comprising:
(a) Program code for reading data items from a database, the data items being generated during a selected time period from monitoring equipment and/or personnel;
(b) Program code for comparing each data item with preset threshold values;

(c) Program code for scoring each of a selected group of functions, each function having a status which is contributory to an overall status of the environment and the number of functions in the group being less than the number of data items, scoring being done on the basis of the comparisons made for all data items indicative of the status of that function;

(d) Program code for converting function scores to a colour representation and assigning these colours to correspondingly scoring functions at the time period, (e) Program code for displaying a series of bar charts on a display screen, wherein each bar chart corresponds to one of the group of functions and comprises a linear series of time-divided segments, and wherein each segment corresponding to the time period on each bar chart is coloured with the colour assigned to the corresponding function.

All these aspects of the invention provide a means with which a wealth of information (data items) can be displayed graphically as a series of coloured bar charts, each bar chart representing the status of a particular contributory factor to the overall condition of the environment. The colours of each bar chart provide a readily assimilated visualisation of both the fluctuating status of each component factor and a quick means of comparison between the various components. In this way, complex assessments can be made more rapidly than known in the prior art.

It is preferred that each bar chart extends horizontally across the display with each successive time period. This arrangement provides a display which is more intuitively understood by a human observer as a time progression chart.

The data items or indicators preferably relate to observations made on the physical condition of a hospital patient. They may, for example, be indicative of one or more of: patient blood pressure, heart rate, temperature, central venous pressure, pulmonary artery catheter data, cardiac output, vascular resistance, urine output, respiratory rate, blood chemistry, haemoglobin, white cells, coagulation profile and arterial blood gases.

Depending on the patient's illness, a sufficient number of organ systems should be selected and displayed to provide an assessment of the patient's overall condition. The functions preferably comprise the functioning of at least two, and preferably at least four of the following organ systems: respiratory, cardiovascular, coagulation, renal, hepatic, neurological and gastrointestinal. Scoring values may be derived for these systems using the Sequential Organ Failure Assessment (or SOFA) scoring system, or a modified version based thereon. Where alternative scoring systems are employed which relate to other major indicators, a selected group of those indicators may be represented by respective bar charts.

It is convenient when using such a system in an intensive care unit for the time period spanned by each segment to be one hour long. Intervals of 15, 20 or 30 minutes may, however, sometimes be preferred.

Although a fixed time base can be used, advantageously the time base is variable, so that the period or interval of the displayed segment can be changed by the viewer, thereby providing a "zoom in" or "zoom out" function. Where the system comprises a plurality of displays that may be selected (usually in place of one another, but possibly also in split screen format), it is usually desirable for a change in the time base in any one display to be reflected in all displays. For example, in the main display, a specific time (e.g. 2 o'clock) may be selected (eg by a cursor), and then the time base may be increased or decreased to display more or less information, the colour of the newly displayed segments being freshly derived from the original data.

Although the clinical display system will usually be associated with an individual patient, it is possible for the system to monitor a plurality of patients simultaneously.

An example embodiment of this invention has been implemented for use in patient assessment in an ICU. The improvement it has brought has been remarkable. In a study made of the responses of nineteen medical and intensive care nursing staff it was found that over six clinical scenarios accuracy of the judgment made as to a patient's status was nearly doubled and the time taken to complete an assessment was reduced by nearly 90% when information was displayed in accordance with this invention rather than as in the prior art patient charts. This, in any situation, represents a dramatic and surprising degree of improvement.

BRIEF DESCRIPTION OF THE DRAWINGS

Non-limiting, example embodiments of the invention will now be described by way of example only and with reference to the accompanying drawings.

Figure 1:
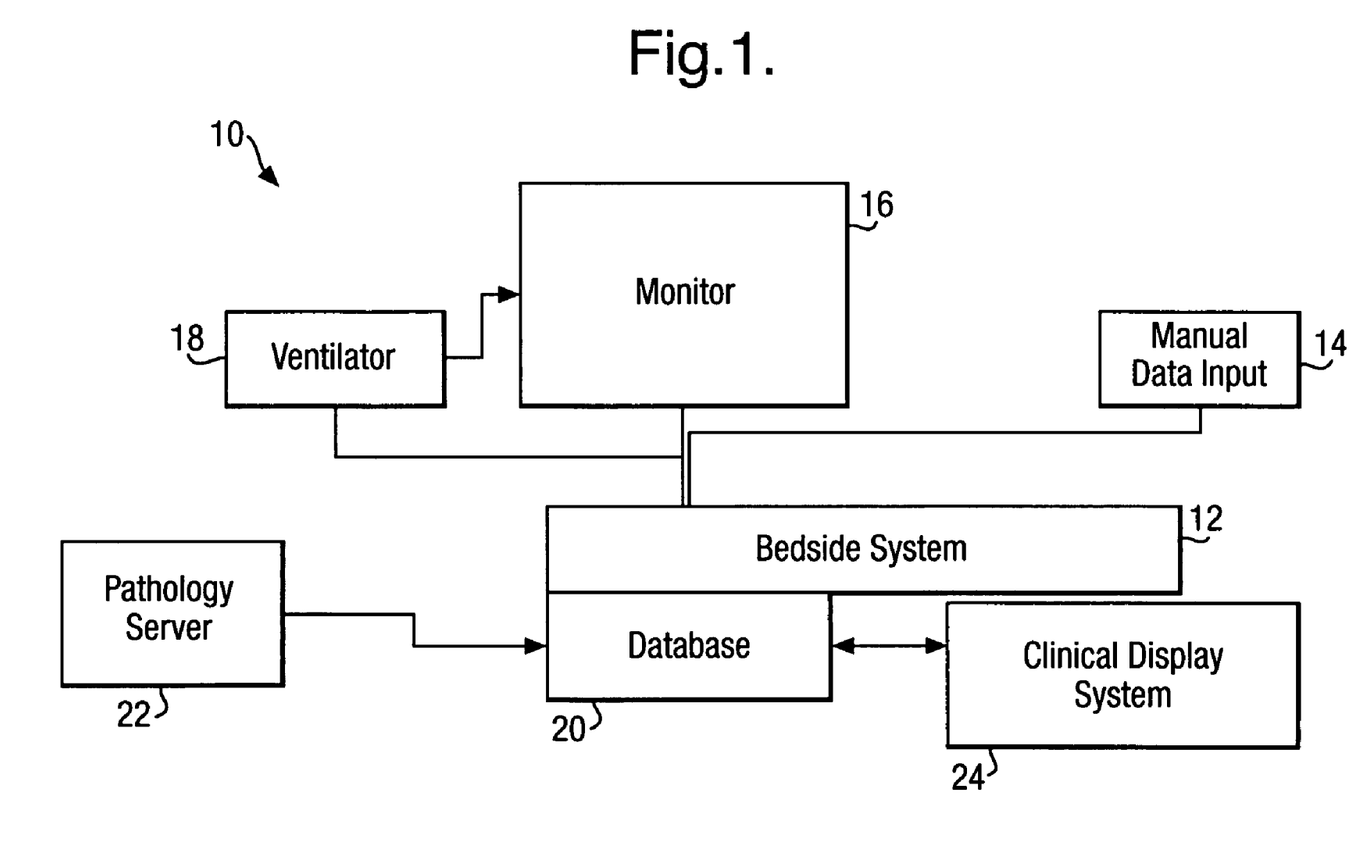
FIG. 1 is a block diagram illustrating equipment used in an intensive care unit with a computer system configured in accordance with an embodiment of this invention.

FIG. 1 illustrates equipment 10 maintained in an intensive care unit (ICU) environment; that equipment may be regarded as a decision support system capable of assisting a clinician at arriving at a decision concerning treatment/discharge, etc of a patient. It is to be noted that the system to be described for use in this environment is a preferred embodiment of the invention, and one skilled in the art will readily appreciate how this embodiment may be adapted for implementation of the invention in alternative data intensive environments.

The equipment 10 comprises a computerised bedside system 12 which collects and stores data relating to a patient from a variety of inputs such as a manual input 14, automated patient monitoring systems 16 and a respiratory ventilator 18. The bedside system 12 is in communication with a database 20, which is populated with data extracted from a pathology server 22 and also from data passed to it from the bedside system 12. A clinical display system 24, which includes a processor (not shown) is arranged to analyse patient information collected by the bedside system 12 and stored in the database 20 in accordance with previously stored data standards.

All the above components, with the exception of the clinical display system are standard commercially available devices. The bedside system 12 comprises a computer running data-gathering software; such software is also readily available in the marketplace. This software enables data capture, storage and manipulation, data being collected both through an automatic interface to standard bedside monitoring equipment 16, 18 and through a manual interface operable by clinical or administrative staff. The patient monitoring systems 16 may include patient support systems that incorporate a monitoring capability. In particular, the patient monitoring systems may include meters, MVO2 devices, cardiac outputs, as well as support devices such as infusion pumps (none shown); thus, there is encompassed any device that traditionally provides information in an ICU which may need to be acted on with urgency.

The database 20 may store, for example, four data types: patient information (i.e. name, date of birth, admission time, etc.), department information (i.e. ward, bed number, consultant in charge, etc), system information (i.e. blood pressure readings, cardiac output, etc) and analysis information (i.e. threshold values for critical indications, conversion values, display characteristics). These data are input or extracted from the various sources 14, 16, 18, 22. It is to be appreciated that whilst the database shown in this preferred embodiment is referred to for convenience as a single database 20, it may in fact comprise a number of physically separate databases, depending on the particular implementation and available equipment. For example, a commercially available bedside system 12 may itself comprise three databases, which store the first three data types. The clinical display system 24 is then configured to include an additional database which stores the analysis information. What is important is the functionality and accessibility of the database(s), not physical location.

Also stored in the database 20 is protocol information, which is text information entered by users. A protocol is a documented description of a process by which a medical intervention is performed. The provision of a defined process by which a treatment is performed facilitates evidence based process improvement and audit. For example, if two alternative protocols for administering a treatment are used for a year in an ICU, and one is found by audit to have a lower risk of subsequent infection, the latter may be solely adopted. The protocol information can be amended as well as deleted, and this may occur through the manual input 14, in order to allow new protocols to be added. The pathology server 22 is a data source which stores the results of pathology laboratory tests and will therefore usually form a separate database. Subject monitoring may therefore involve the remote processing of samples from the subject, and those results may be retrieved by electronic transfer or input manually.

When the system is in use, the status of a critically ill patient is constantly checked both by means of readings taken automatically by the monitoring system 16 and also usually by manual tests and observations made by trained staff. Monitoring system measurements are input to the bedside system 12 via the automatic interface and these data are supplemented by the manual test results entered onto the system 12 via the manual data input 14. Such measurements and results will include, for example, information concerning blood pressure, heart rate, temperature, central venous pressure, pulmonary artery catheter data, cardiac output, vascular resistance, urine output, respiratory rate and, if the patient is on a ventilator, the amount of oxygen dispensed, the ventilatory pressure, PEEP, together with laboratory data relating to blood chemistry (some 14 variables), haemoglobin, white cells, coagulation profile (4 variables) and the variables (6) estimated from arterial blood gases. Some of these data are collected every 15 minutes, some on an hourly basis and others several times a day. Together, all this data comprises the information which was traditionally recorded on a chart beside the patient's bed. In this embodiment of the invention, this data, which can be seen to be tracking the progress of the patient is captured electronically and stored in the database 20 of the system 10.

In addition, in contrast to prior art systems, all interventions and manoeuvres undertaken by a doctor or nurse for a patient under their care are entered on the system 12 via the manual input 14. Such interventions will follow one of a number of the pre-recorded protocols described above. Alternatively, any non-standard interventions will be recorded as usual, and, in addition, the associated protocol will be entered on the database 20. This completes the electronic record for an individual patient. Both progress data and treatment data together constitute a stream of patient information that is stored in the database 20 for processing by the clinical display system (CDS) 24. After processing, the CDS 24 displays the information in a format that better facilitates its use by doctors and nurses to improve their management of the seriously ill patients under their care.

Traditionally, doctors and nurses have used their skill and experience in interpreting the wealth of information presented on a patient's chart. Attempts have been made to codify the largely intuitive assessment made by these skilled clinicians. One scoring system which has been developed over the past 10 to 15 years is the Sequential Organ Failure Assessment, or SOFA. This system, which has been extensively validated and is widely accepted, is based on the finding that patient outcome is strongly correlated to the number of dysfunctioning organs. A systematic interpretation of chart data is used to provide some indication of which of the major organs are liable to fail, an approach which is routinely taught to trainee doctors and nurses.

The SOFA scoring system assigns a score within a range from 0, indicating normal function, to 4, indicating severe dysfunction, to each of the major organ systems. The CDS 24 is programmed and configured to implement a modified SOFA and to display the results on a screen. The CDS SOFA additionally includes an assessment of the gastrointestinal system, based on the criteria of feeding method and attainment of target feed rate. In total therefore the CDS 24 performs an automatic scoring assessment of each of seven major organ systems (including gastrointestinal). After scoring each organ system, the CDS 24 prepares the results for display.

A GENERAL status indicator may also be displayed, to enable the clinician to display one or more selected measured (or observed and manually input) parameters that they associate with the subject's overall status. This is not defined by an established scoring system, but rather is derived on an implementation basis by those responsible for the system. For example, the patient's lactose level may be measured and displayed.

Figure 2:
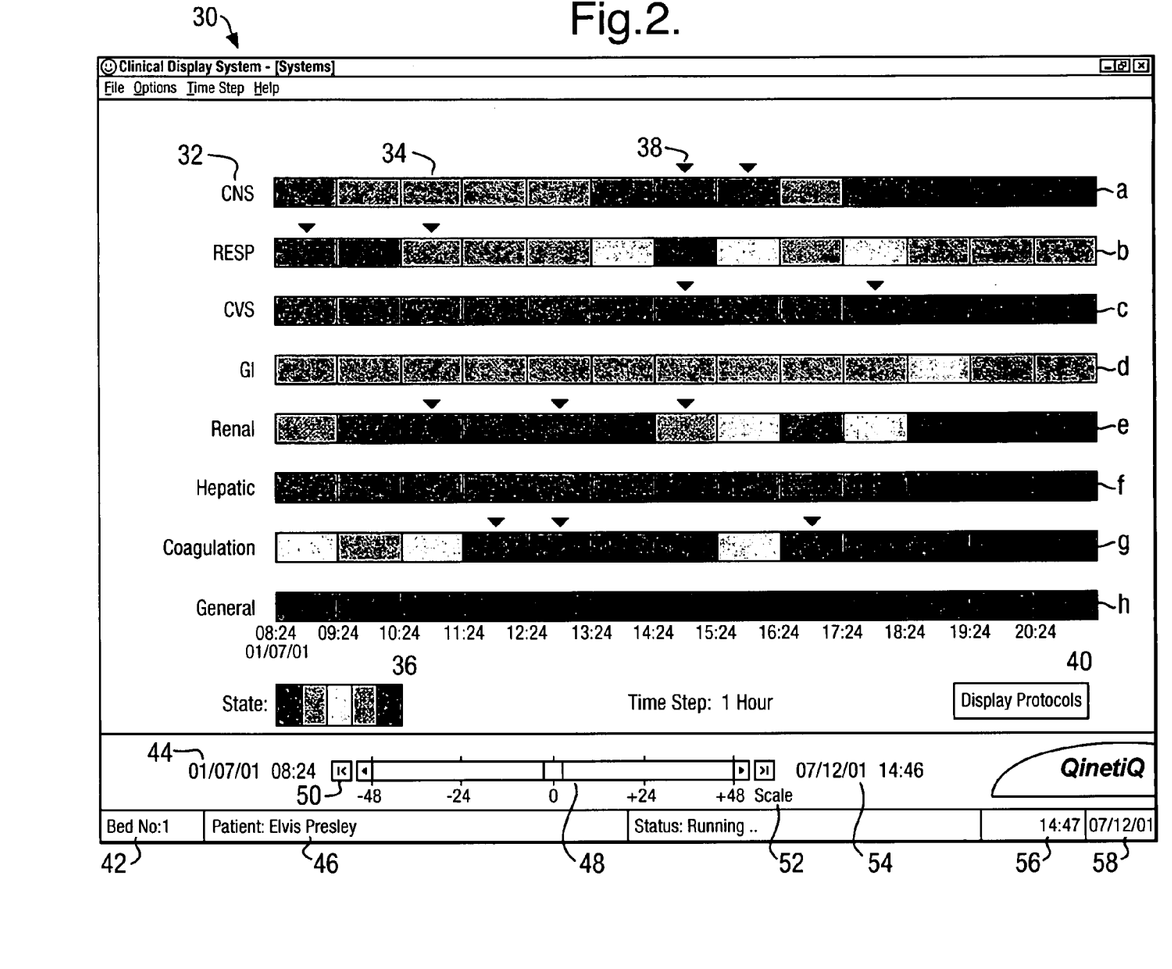
FIG. 2 is an exemplary output screen generated by the computer system embodiment of FIG. 1.

An example of a display output from the CDS 24 is shown in FIG. 2. The display 30 consists of eight time bars (a to h) divided into hours. Each monitored organ system 32 is listed on the display 30 adjacent a corresponding single bar. The eighth bar h is used to display the general patient condition. Within each band a–h, each hour segment 34 is colour coded to reflect the status of the particular organ system 32 being monitored within that time frame. A key 36 to the colour coding is presented at the bottom left of the display 30 and in Table 1 below.

TABLE 1

| Colour | Status |
| --- | --- |
| Dark green | System is normal |
| Light green | Mild dysfunction |
| Yellow | Mild/moderate dysfunction |
| Orange | Moderate/severe dysfunction |
| Red | Severe dysfunction |

Also present on the display 30 are intervention indicators 38 and a button 40 on which to click a mouse cursor (not shown) for access to a protocol display screen, which will be described later. Patient information such as bed number 42, admission time 44 and name 46 are displayed at the bottom left of the screen 30. A scroll bar 48 may be used to adjust the time frame of displayed information, with separate buttons 50, 52 to allow jumps to patient admission time and to most recent time data. To the bottom right of the screen 30 time of the last CDS update 54 and present time 56 and date 58 are displayed.

The seven systems 32 for which the CDS 24 displays information are the central nervous system (written on screen as CNS), corresponding to the neurological SOFA indicator, respiratory system (written as RESP), cardiovascular system (CVS), corresponding to the circulatory SOFA indicator, and the gastrointestinal (GI), renal, hepatic, and coagulation systems, the latter corresponding to the haematological SOFA indicator; a general condition status indicator may also be displayed, as discussed above.

In this way the CDS is arranged to display clearly and concisely indications as to the status of each major organ system 32 of a critically ill patient over a period of time. Changing colours on each indicator bar a–h, provide a doctor or nurse with a rapidly assimilated indication as to whether each organ's status is improving or failing.

The intervention indicators 38 are placed on a time line above selected bar charts a–h. An intervention is a procedure which may be performed by a doctor or nurse with the aim of improving the patient's condition. A significant proportion of interventions will be scheduled events, although some will be random events made in response to a change in the patient's state. The placing of the indicator on the time line therefore provides a clearly visible indication of the time at which an intervention has been made. The bars a–h it appears adjacent to are those displaying the status of the organ system(s) that the particular intervention is known to affect. In this way, it may be readily confirmed whether or not its intended result, in terms of an improvement of a particular organ's status, is achieved. Each time period may have only one intervention symbol 38 above it, although obviously a number of different procedures may have been tried. However the CDS 24 is arranged such that an intervention window may be opened by clicking a mouse cursor on the intervention symbol 38. The window contains information as to the number and type of interventions made as well as any further information recorded by the clinician; for example timings, reasons and action taken. This window also provides a further access route identifying the relevant protocol(s) used in the intervention(s).

Figure 3:
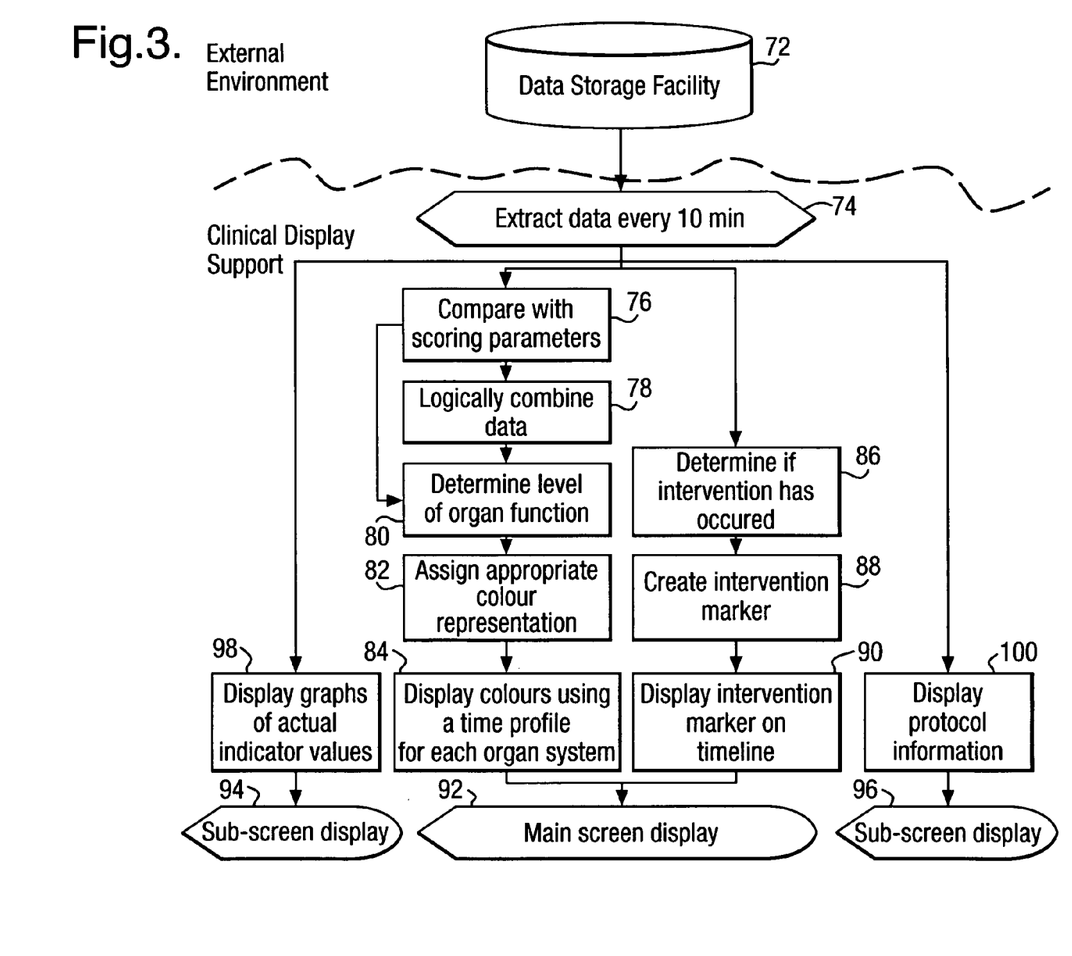
FIG. 3 is a functional diagram indicating the process steps carried out by the computer system of FIG. 1 in implementing a second aspect of the invention.

FIG. 3 is a functional diagram indicating the process steps carried out by the CDS 24 in generating the display 30 of FIG. 2. External to the CDS 24 is a data storage facility 72 (corresponding to the database 20 of FIG. 1). At selected intervals, here every 10 minutes, the CDS 24 performs step 74 and extracts data from this storage facility 72. In this way the CDS 24 is kept updated with the most recently taken patient information. At step 76, the extracted data is compared with preset scoring parameters and a score is derived from that data for each organ system. For example, one test result which is included in the extracted data will be information as to the creatinine level in the patient's blood. If this level is greater than 440 mcgmol/l (µgmol/l) this is indicative of severe dysfunction of the renal system and scores 4 (using the SOFA scoring scale from 0, indicating normal level to 4 indicating severe dysfunction). On the other hand, if the measured creatinine level is between 100 and 170 mcgmol/l, this is indicative of a mildly dysfunctional renal system and scores 1. The complete scoring parameters across the organ systems and as used in this embodiment of the invention are indicated in Appendix 1.

At step 78 the status indicators derived in step 76 are, if necessary, logically combined. Logical combinations are required when the scoring system dictates that there are two or more data items needed to assess the current function of a particular organ system. Each data item has been evaluated and scored individually at step 76. If the data items needed for one organ system assessment differ in their assigned scores, the function of the organ system is considered to be that of the worst case. For example, analysis of the renal system involves both the assessment of blood creatinine and daily urine output. If the creatinine level is between 100 and 170 mcgmol/l and therefore scoring 1 (as described above) and the daily urine output is less than 200 ml, which indicates a severe dysfunction of the renal system and scores 4, logical combination will result in an overall score of 4. This function is defined as 'Logical Inclusive OR'. However, the system may be adapted to support the full range of logical and mathematical functions that could be employed in the assessment of a combination of individual factors both relatively or absolutely.

At step 80, for each respective organ system 32, its level of function is determined. Thus, using the example of the renal system, its score with the data values given above is 4 for the relevant time period. Other systems make use of different data indicators, which may or may not need to be combined, and a system score is derived at this step 80 each.

At step 82 each score is assigned an appropriate colour representation. From Table 1, it can be seen that a score of 4 for the renal system means the assigned colour to indicate renal status is red. For each status bar a–h, an additional colour segment block is then added to the display 30 at step 84, each block being placed at the appropriate point of the timeline and given the status indicator colour derived at step 82.

The individual bar charts have time-divided segments arranged abutting one another so that the bar extends continuously from left to right along a timeline. The bar chart therefore appears to the eye of the beholder to provide a continuous representation of the patient's state, when in fact each time segment is displaying the state of that organ at a particular selected point in time (corresponding to the time interval selected). Thus, in contrast to prior art continuous displays, no assumption is made by the display of the data values between the interval times which is significant when the time interval exceeds the contributing data sample rates and not all changes in state are shown although the display appears continuous. In contrast to the prior art, the system incorporates variable "data persistence" facilitating the evaluation of less frequently sampled data with more frequently sampled data where the data sample rate can be adjusted to a time consistent with the data change rate; this "data persistence" element of the display improves intelligibility for the clinician.

Concurrently with the status colour determination, the CDS 24 is also arranged to carry out a number of other processes. From the data extracted at step 74, at step 86 the CDS 24 checks whether there has been a clinical intervention. If the result is positive, an intervention marker is created at step 88 and displayed 90 at the appropriate point on the timeline (see, for example, symbol 38 of FIG. 2).

The intervention marker and coloured time profile for each organ system are the only processes carried out by the CDS 24 the results of which are displayed on a main screen display 92, as shown in FIG. 2. However an additional two sub-screen displays 94, 96 are also created by the CDS 24 and may be accessed via the main screen display 92.

Figure 4:
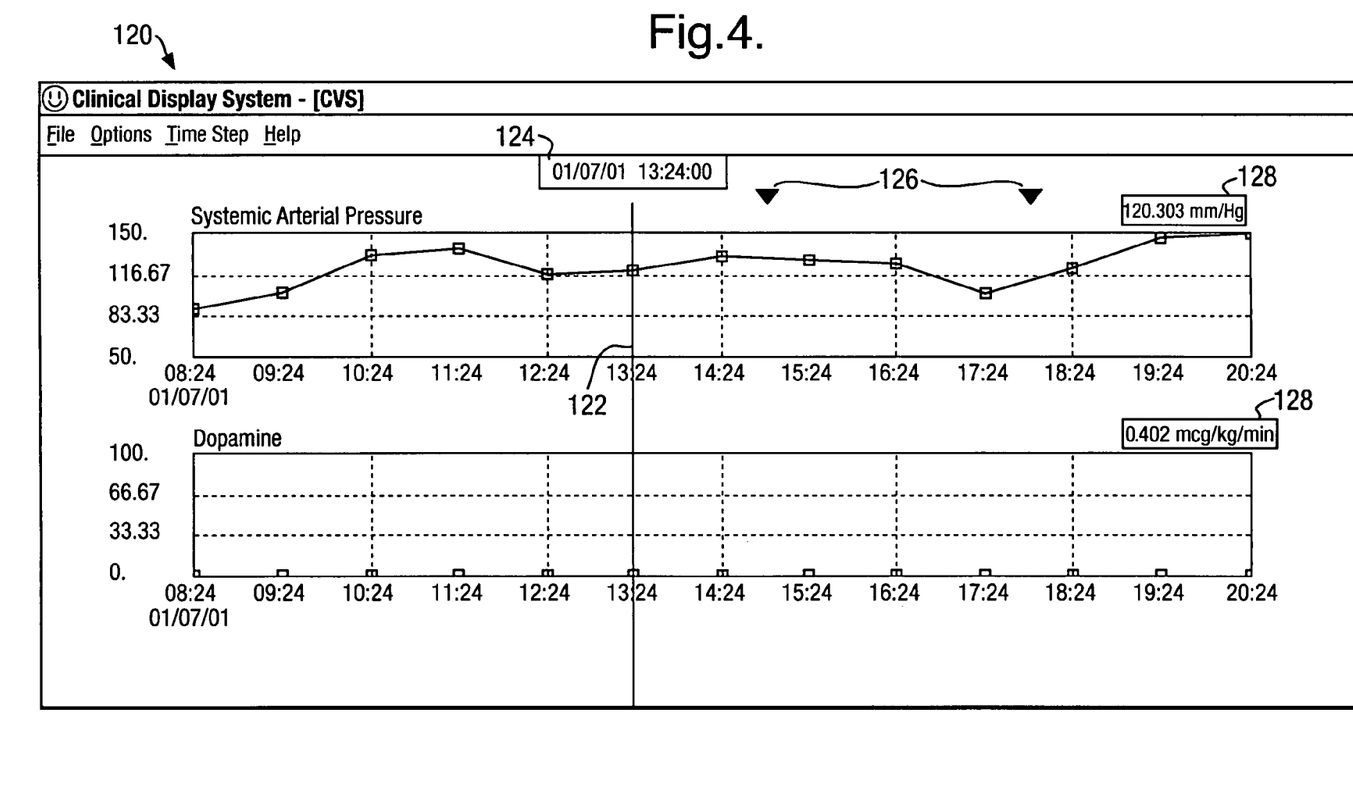
FIG. 4 is an exemplary subscreen display indicating actual data values used to derive one of the bar charts of FIG. 2.

The first of these subscreen derivations is indication at step 98. At this step the CDS 24 derives for each data type (individual reading) extracted from the database 20 at step 74, a graphical display of actual values of that reading against time. For each data type, this graph is displayable on respective subscreens 94 which are accessible from the main display 92 by double clicking on the relevant segment of the organ system concerned: all the data type readings associated with that organ system are simultaneously displayed on subscreen 94. The subscreen may have a data cursor for selecting the display of individual values in the data value windows on the detailed display. Where displayed the cursor is the time point about which the display is redrawn in the event of the time scale being altered. FIG. 4 is an example of such a graphical display showing a patient's mean arterial pressure and dopamine levels If protocol information is requested, the CDS 24 at step 100, extracts it from the database 20 for display on a second subscreen 96. Protocol screens can be accessed from the main display 30 with button 40. At any given time, clinical staff can access detailed protocol information for any given organ system. An example of a protocol screen is shown in FIG. 5.

Referring to FIG. 4 (showing an example of the first subscreen display), there is shown a graphical display 120 of actual indicator values for the cardiovascular system. The relevant indicators for this system are systemic arterial blood pressure and inotrope (for example dopamine) levels. A blue cursor 122 is activated by clicking the mouse on the graph and, above the cursor position are shown date and time 124 that the highlighted data value was measured and, to the right of the graph, the actual values 128 recorded at that time. Interventions 126, if any, are also shown on this display 120.

Accessing this display enables a skilled clinician to investigate further indicators as to the functioning of any particular organ system.

Figure 5:
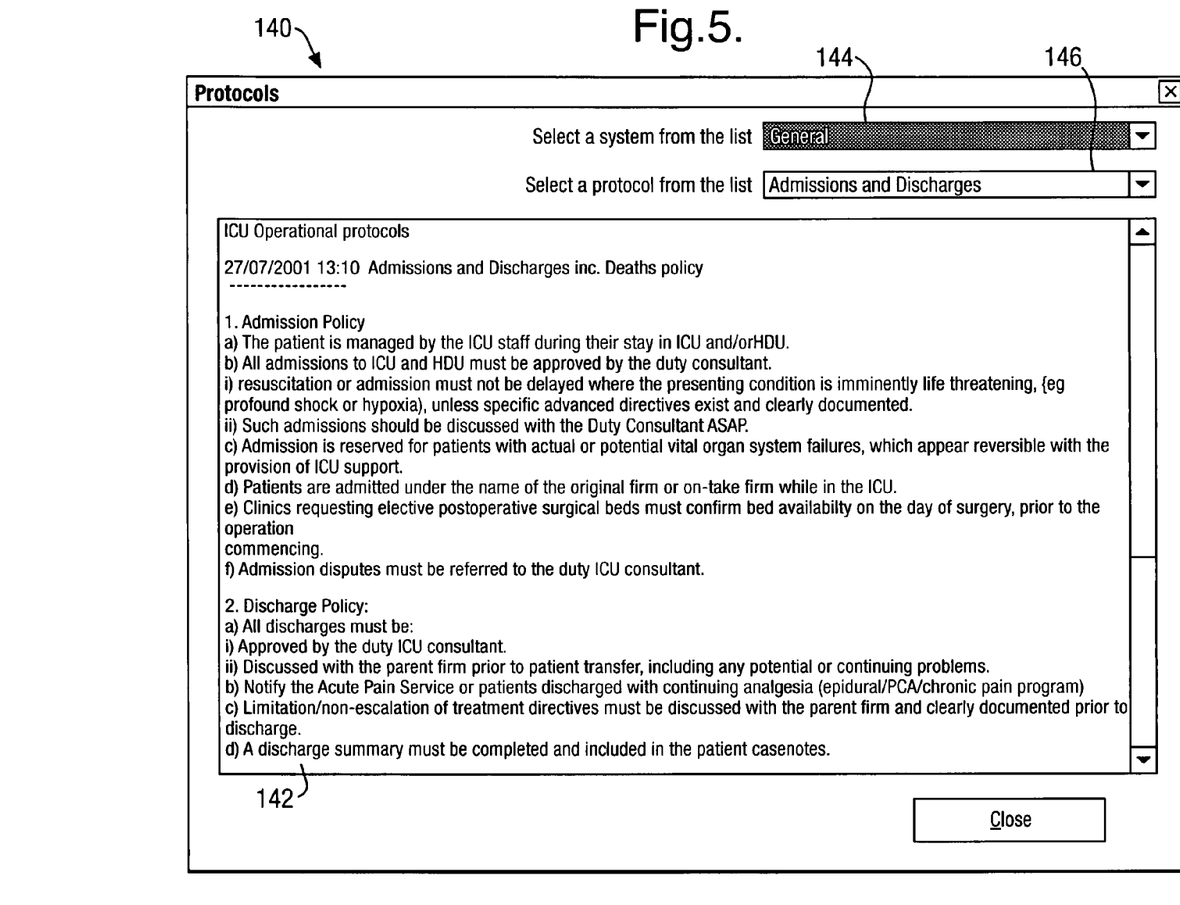
FIG. 5 is an exemplary subscreen display of a protocol screen, which is generated by the computer system of FIG. 1.

FIG. 5 illustrates an example of a protocol display 140. Protocol information 142 is displayed on the screen once one of the eight systems (organs and general) 32 have been selected from a first drop down box 144 and a particular protocol is selected from a second drop down box 146.

Figure 6:
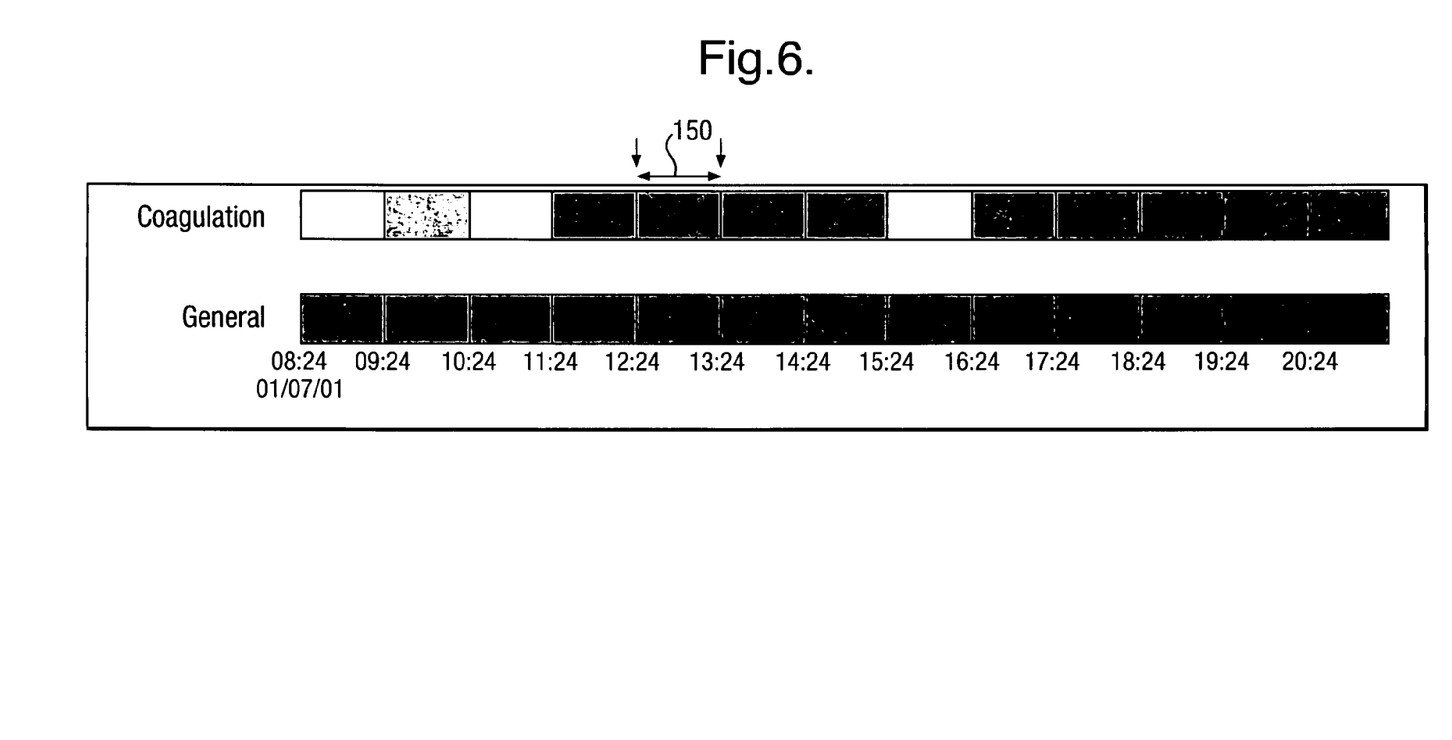
FIG. 6 is an expanded view of one of the bar charts of FIG. 2.

FIG. 6 is an expanded view of the coagulation indicator bar g, shown in FIG. 2. It illustrates more clearly the segmented coloured blocks which provide for rapid visual assimilation of information by the clinician. A double headed arrow 150 indicates the length of time period covered by each block. A default value for this embodiment of the invention is one hour, but the CDS 24 is arranged to permit this to be amended by means of a menu which appears when a mouse is right-clicked above any system bar a–h.

In this system software algorithms filter the extracted data using a clinically agreed scoring system which involves some logical combinations. As mentioned previously this embodiment of the invention uses a modified SOFA system to present a visualisation of the status of a patient. It will be clear to one skilled in the art however that other algorithms implementing other known scoring systems can also be used as intelligence filters. Appendix 2 lists a number of other established scoring systems which may be used in accordance with the present invention.

Equally, the invention may be of assistance in assessing the status of animal patients.

Further, it will also be appreciated by one skilled in the art that this invention is not limited to application in an intensive care unit, but to any situation in which a judgment has to be made based on interpretation of a vast amount of data. It is particularly applicable to environments that require tracking of multi-system functioning. In a clinical environment these may be high dependency wards (using discharge criteria as a scoring system), general wards (clinical state of a patient could provide a scoring system) and home monitoring (using custom scoring values). Other environments where the application of this invention may prove useful is to factories, power stations and water treatment plants.

Further applications may be found in auditing and resource management.

Appendix 1

Clinical Display System SOFA Threshold Levels

APPENDIX 1

Clinical Display System SOFA threshold levels

| Organ System | Vital Sign | State | Threshold | Unit |
|---|---|---|---|---|
| Central Nervous System | Glasgow Coma Score | 0 | 15 | Points |
|  |  | 1 | <15 |  |
|  |  | 2 | <13 |  |
|  |  | 3 | <9 |  |
|  |  | 4 | <6 |  |
| Respiratory | PaO2/FIO2 | 0 | >=53 | kPa |
|  | FIO2(0.21–1.0) | 1 | <53 |  |
|  |  | 2 | <40 |  |
|  |  | 3 | <27 |  |
|  |  | 4 | <13 |  |

APPENDIX 1-continued

Clinical Display System SOFA threshold levels

| Organ System | Vital Sign | State | Threshold | Unit |
|---|---|---|---|---|
| Cardiovascular | Mean Arterial Pressure | 0 | >=70 | mmHg |
| | | 1 | <70 | |
| | Inotropes | 2 | Use of Dopexamine <= 0.5 Use of Dopamine <= 5.0 Use of Dobutamine | mcg/kg/min |
| | | 3 | Any of the following: Dopexamine > 0.5 Dopamine > 5.0 Noradrenaline < 0.1 Adrenadine < 0.1 | |
| | | 4 | Any of the following: Dopexamine > 1.5 Dopamine > 5.0 Noradrenaline > 0.1 Adrenadine > 0.1 Use of Milrinone | |
| Gastro-Intestinal | Nutrition type | 0 | Diet/Target feed rate attained | |
| | | 1 | 51–99% of target feed rate | |
| | | 2 | 20–50% of target feed rate | |
| | | 3 | <20% of target feed rate | |
| | | 4 | On TPN or IV fluids only | |
| Renal | Creatinine | 0 | <100 | mcgmol/l |
| | | 1 | <=170 | |
| | | 2 | <300 | |
| | | 3 | <440 | |
| | | 4 | >440 | |
| | Urine Output | 0 | >500 | mls/24 Hrs |
| | | 1 | N/A | |
| | | 2 | N/A | |
| | | 3 | <500 | |
| | | 4 | <200 | |
| Hepatic | Bilirubin | 0 | <=20 | mcgmol/l |
| | | 1 | >20 | |
| | | 2 | >34 | |
| | | 3 | >102 | |
| | | 4 | >204 | |
| Coagulation | Platelet level | 0 | >=150 | E9/l |
| | | 1 | <150 | |
| | | 2 | <100 | |
| | | 3 | <50 | |
| | | 4 | <20 | |

State 0 - Normal
State 1 - Mild dysfunction
State 2 - Mild/Moderate dysfunction
State 3 - Mod/Severe dysfunction
State 4 - Severe dysfunction

Appendix 2

Established Scoring Systems
  Adults
  General scores
  SAPS II and predicted mortality
  APACHE II and predicted mortality
  MODS (Multiple Organ Dysfunction Score)
  ODIN (Organ Dysfunctions and/or INfection)
  Pediatrics
  General scores
  PRISM (Pediatric RISk of Mortality)
  DORA Dynamic Objective Risk Assessment)
  PELOD (Pediatric Logistic Organ Dysfunction)
  PIM (Paediatric Index of Mortality)
  Adult
  Specialized and Surgical Intensive Care—Preoperative Evaluation
   EUROSCORE (cardiac surgery)
   ONTARIO (cardiac surgery)
   Parsonnet score (cardiac surgery)
   System 97 score (cardiac surgery)
   QMMI score (coronary surgery)
   MPM for cancer patients
   POSSUM (Physilogic and Operative Severity Score for the enUmeration of Mortality and Morbidity) (surgery, any)
   Portsmouth POSSUM (surgery, any)
   Specialized (Neonatal, Surgical)
   CRIB (Clinical Risk Index for Babies)
   Snap (Score for Neonatal Acute Physiology)
   SNAP-PE (SNAP Perinatal Extension)
   SNAP II and SNAPPE II
   Adult Trauma Scores
   ISS (Injury Severity Score), RTS (Revised Trauma Score), TRISS (Trauma Injury Severity Score)
   ASCOT (A Severity Characterization Of Trauma)
   24 h-ICU Trauma Score
   Pediatric Trauma Scores
   Pediatic Trauma Score
   Therapeutic Intervention, Nursing ICU Scores TISS (Therapeutic Intervention Scoring System)

The invention claimed is:

1. A method of analysis of data measured in a time-varying environment, the method comprising the steps of:
   (a) recording data items generated during a selected time period from both monitoring equipment and recording intervention data entered by personnel;
   (b) comparing each data item recorded at step (a) with preset threshold values;
   (c) selecting a group of functions, each function having a status which is contributory to an overall status of the environment and the number of functions in the group being less than the number of data items, scoring each function on the basis of the comparisons made at step (b) for all data items indicative of the status of that function;
   (d) converting scores obtained at step (c) to a color representation and assigning these colors to correspondingly scoring functions at the time period,
   (e) displaying a series of bar charts on a display screen, wherein each bar chart corresponds to one of the group of functions and comprises a linear series of time-divided segments, and wherein each segment corresponding to the time period on each bar chart is colored with the color assigned to the corresponding function at step (d); and
   (f) repeating steps (a) to (e) for an adjacent time period, while preserving bar chart segment coloration for at least one previous time period,
   wherein the data items relate to the physical condition of a patient and the group of functions comprise the functioning of six of respiratory, cardiovascular, coagulation, renal, hepatic, neurological systems, and gastrointestinal systems.

2. A method according to claim 1 wherein the group of functions comprise the functioning of all seven of the respiratory, cardiovascular, coagulation, renal, hepatic, neurological systems, and gastrointestinal systems.

3. A method according to claim 1 wherein the scoring step is carried out in accordance with a Sequential Organ Failure Assessment (SOFA) scoring system, or a modified version thereof.

4. A method according to claim 1 wherein bar chart segment coloration is preserved for at least 8 previous time periods.

5. A method according to claim 4 wherein each time period is one hour long.

6. A method according to claim 4 wherein each bar chart extends horizontally across the display with each successive time period.

7. A computer system programmed to provide a graphical display of derived information, the display comprising a series of bar charts representative of a corresponding series of functions, each bar chart comprising a linear series of time-divided segments, wherein each segment of each bar chart is one of a set of permitted colors; to assign the colors to the segments in accordance with the status of the corresponding function at the time period represented by that segment; and to derive the status of each function from a number of data indicators extracted from a database, wherein each data indicator comprises an experimental observation made on a system at a time corresponding to the time period represented in the bar chart by the relevant segment, and the status of each function is derived by scoring contributory data indicators in accordance with preset threshold values to produce a status score for each function,
wherein the data indicators include data relating to data items read from a database, the data items comprising data generated during a selected time period from monitoring equipment and intervention data entered by personnel,
wherein the data items relate to the physical condition of a patient and the group of functions comprise the functioning of six of respiratory, cardiovascular, coagulation, renal, hepatic, neurological systems, and gastrointestinal systems.

8. A computer system according to claim 7 wherein the data indicators comprise observations made on a hospital patient.

9. A computer system according to claim 8 wherein the data indicators comprise information indicative of at least one of patient blood pressure, heart rate, temperature, central venous pressure, pulmonary artery catheter data, cardiac output, vascular resistance, urine output, respiratory rate, blood chemistry, hemoglobin, white cells, coagulation profile and arterial blood gases.

10. A computer system according to claim 7 wherein the status of each function is derived from the data indicators in accordance with one of a Sequential Organ Failure Assessment (SOFA) scoring system, or a modified SOFA scoring system.

11. A subject monitoring system which graphically displays derived information, the system comprising:
   monitoring equipment arranged to make periodic observations on said subject, a database arranged to store as data items results of periodic observations made by the monitoring equipment,
   manual data input equipment arranged to enable entering and recording of intervention data in the database;
   a processor arranged to analyze periodically the stored data items to provide an indication as to status of a selected group of functions, the status of each function being deducible as a score from a subset of the data items compared with preset threshold values, and
   a display arranged to display a series of bar charts representative of the group of functions, each bar chart comprising a linear series of time-divided segments wherein each segment of each bar chart is one of a set of permitted colors, the colors being assigned to the segments in accordance with the score obtained for the corresponding function at the time period represented by that segment and to display data representative of the intervention data,
   wherein the monitoring equipment comprise medical monitoring equipment and said subject is a patient and the functions comprise the functioning of six of respiratory, cardiovascular, coagulation, renal, hepatic, neurological systems, and gastrointestinal systems.

12. A monitoring system according to claim 11, wherein the data indicators comprise information indicative of at least one of patient blood pressure, heart rate, temperature, central venous pressure, pulmonary artery catheter data, cardiac output, vascular resistance, urine output, respiratory rate, blood chemistry, hemoglobin, white cells, coagulation profile and arterial blood gases.

13. A monitoring system according to claim 11, wherein the status of each function is derived from the data indicators in accordance with a Sequential Organ Failure Assessment (SOFA) scoring system, or a modified SOFA scoring system.

14. A programmable digital computer, said computer programmed for:
- (a) reading data items from a database, the data items comprising data generated during a selected time period from monitoring equipment and intervention data entered by personnel;
- (b) comparing each data item with preset threshold values;
- (c) scoring each of a selected group of functions, each function having a status which is contributory to an overall status of the environment and the number of functions in the group being less than the number of data items, said scoring on the basis of the comparisons made for all data items indicative of the status of that function;
- (d) converting function scores to a color representation and assigning these colors to corresponding scoring functions in the time period; and
- (e) displaying a series of bar charts on a display screen, wherein each bar chart corresponds to one of the group of functions and comprises a linear series of time-divided segments, and wherein each segment corresponding to the time period on each bar chart is colored with the color assigned to the corresponding function, wherein the data items comprise observations made on a patient and the group of functions comprise the functioning of six of respiratory, cardiovascular, coagulation, renal, hepatic, neurological systems, and gastrointestinal systems.

15. A programmable digital computer according to claim 14, wherein the data items comprise information indicative of at least one of patient blood pressure, heart rate, temperature, central venous pressure, pulmonary artery catheter data, cardiac output, vascular resistance, urine output, respiratory rate, blood chemistry, hemoglobin, white cells, coagulation profile and arterial blood gases.

16. A programmable digital computer according to claim 14, wherein the status of each function is derived from the data indicators in accordance with a Sequential Organ Failure Assessment (SOFA) scoring system or a modified SOFA scoring system.

17. A method of analysis of data measured in an environment that varies with time, the method comprising the steps of:
- (a) recording data generated during selected time interval(s) from monitoring equipment and intervention data entered by personnel;
- (b) comparing each data item gathered at step (a) with preset threshold values;
- (c) for each of a selected group of functions, each function having a status which is contributory to an overall status of the environment and the number of functions in the group being less than the number of data items, scoring each function on the basis of the comparisons made at step (b) for all data items indicative of the status of that function;
- (d) converting scores obtained at step (c) to one of a number of selected visual representations and assigning those representations to correspondingly scoring functions for a specific time period;
- (e) recording at least one intervention conducted upon, and capable of affecting, the environment;
- (f) displaying a series of graphical representations on a display screen, wherein each graphical representation corresponds to one of the group of functions and comprises a series of time-divided segments arranged sequentially, and wherein each segment corresponding to the time period on each graphical representation is visually represented according to the visual representation assigned to the corresponding function at step (d);
- (g) displaying on the display screen the at least one intervention adjacent to at least one of the segments corresponding to the time of the intervention and adjacent to a timeline corresponding to the time-divided segments so as to facilitate a comparison of the effect of the intervention on the environment; and
- (h) repeating steps (a) to (e) for an adjacent time period, whilst preserving the segment's visual representation for at least one previous time period, wherein the data relates to the physical condition of a patient and the group of functions comprise the functioning of six of respiratory, cardiovascular, coagulation, renal, hepatic, neurological systems, and gastrointestinal systems.

18. A method of analysis according to claim 17, wherein the intervention is displayed against the segments of at least one of the functions that said intervention is capable of affecting.

19. A method of analysis according to claim 17, wherein the intervention is displayed as at least one of selected details and a marker.

20. A method of analysis according to claim 18, in which a marker is solely employed, but further details of the intervention are accessible for display by the user.

21. A method of analysis according to claim 16, wherein a protocol by which an intervention is conducted is additionally recorded and is at least displayed or accessible for display by the user.

22. A program product for a computer stored on a machine-readable medium, said program product comprising code portions for:
- (a) reading data items from a database, the data items comprising data generated during a selected time period from monitoring equipment and intervention data entered by personnel;
- (b) comparing each data item with preset threshold values;
- (c) scoring each of a selected group of functions, each function having a status which is contributory to an overall status of the environment and the number of functions in the group being less than the number of data items, scoring being done on the basis of the comparisons made for all data items indicative of the status of that function;
- (d) converting function scores to a color representation and assigning these colors to corresponding scoring functions in the time period,
- (e) displaying a series of bar charts on a display screen, wherein each bar chart corresponds to one of the group of functions and comprises a linear series of time-divided segments, and wherein each segment corresponding to the time period on each bar chart is colored with the color assigned to the corresponding function, wherein the data items comprise observations made on a patient and the group of functions comprise the functioning of six of respiratory, cardiovascular, coagulation, renal, hepatic, neurological systems, and gastrointestinal systems.

* * * * *